(12) United States Patent
Haudenschild

(10) Patent No.: US 7,509,280 B1
(45) Date of Patent: Mar. 24, 2009

(54) ENTERPRISE HEALTHCARE MANAGEMENT SYSTEM AND METHOD OF USING SAME

(75) Inventor: Chris A. Haudenschild, La Jolla, CA (US)

(73) Assignee: ClinlComp International, Inc., San Diego, CA (US)

( * ) Notice: Subject to any disclaimer, the term of this patent is extended or adjusted under 35 U.S.C. 154(b) by 0 days.

(21) Appl. No.: 09/358,355

(22) Filed: Jul. 21, 1999

Related U.S. Application Data

(63) Continuation-in-part of application No. 09/358,355, filed on Jul. 21, 1999, which is a continuation-in-part of application No. 08/977,522, filed on Nov. 24, 1997, now Pat. No. 6,401,072.

(51) Int. Cl.
G06Q 40/00 (2006.01)
(52) U.S. Cl. .............................. 705/37; 705/35; 705/36; 705/38
(58) Field of Classification Search ................. 705/1–4, 705/35–38, 17; 707/10, 100–104
See application file for complete search history.

(56) References Cited

U.S. PATENT DOCUMENTS

| | | | |
|---|---|---|---|
| 4,893,270 A * | 1/1990 | Beck et al. | |
| 5,193,855 A | 3/1993 | Shamos et al. | 283/117 |
| 5,262,943 A | 11/1993 | Thibado et al. | 364/413.01 |
| 5,558,638 A * | 9/1996 | Evers et al. | |
| 5,694,552 A * | 12/1997 | Aharoni | 705/37 |
| 5,771,354 A | 6/1998 | Crawford | |
| 5,781,442 A * | 7/1998 | Engleson et al. | 700/214 |
| 5,812,983 A | 9/1998 | Kumagai | 705/3 |
| 5,823,948 A | 10/1998 | Ross | 600/300 |
| 5,845,253 A | 12/1998 | Rensimer | 705/2 |
| 5,857,967 A | 1/1999 | Frid | 600/301 |
| 5,867,821 A * | 2/1999 | Ballantyne et al. | 705/2 |
| 5,903,889 A * | 5/1999 | de la Huerga et al. | 705/3 |
| 5,918,229 A * | 6/1999 | Davis et al. | 707/10 |
| 5,933,809 A * | 8/1999 | Hunt et al. | 705/3 |

(Continued)

FOREIGN PATENT DOCUMENTS

JP 408180120 A * 7/1996

OTHER PUBLICATIONS

Suzan Eich, "Honeywell Introduces Computers Network Facility for Hospitals", Jul. 29, 1985, Dialog file 621, Accession No. 00102603.*
"Extensible Access Control List Mechanism", IBM Technical Disclosure Bulletin, Dec. 1991, vol. 34, Issue No. 7B, TDB-ACC-No. NB9112114.*

(Continued)

*Primary Examiner*—Frantzy Poinvil
*Assistant Examiner*—Clement Graham
(74) *Attorney, Agent, or Firm*—Bernard L. Kleinke; Duckor Spradling Metzger & Wynne

(57) ABSTRACT

The enterprise healthcare management system and method includes a novel healthcare management system. The healthcare management system includes a server system connected to a plurality of enterprise facilities. A master index and a shared document repository on the server facilitate positively identifying patients and confidently associating that patient with proper medical records. The method of using the system also facilitates finding where in the enterprise a patient is located, and identifying available patient records. Healthcare practitioners also use the healthcare management system to access a patient treatment plan system, irrespective of which enterprise facility presently has the patient or which enterprise treatment plan system operates the patient treatment plan.

30 Claims, 9 Drawing Sheets

U.S. PATENT DOCUMENTS

| | | | | |
|---|---|---|---|---|
| 6,005,962 | A | | 12/1999 | Hirota et al. ............... 382/124 |
| 6,014,643 | A | * | 1/2000 | Minton ........................ 705/37 |
| 6,151,588 | A | * | 11/2000 | Tozzoli et al. ................ 705/37 |
| 6,157,914 | A | * | 12/2000 | Seto et al. ...................... 705/3 |
| 6,607,485 | B2 | * | 8/2003 | Bardy ........................ 600/300 |

OTHER PUBLICATIONS

Health Records Canadian Health Facilities Law Guide. North York: Nov. 24, 1997. , Iss. 18; p. 1.*

Virtual Hospital Presentation and Outline.

* cited by examiner

ENTERPRISE HEALTHCARE MANAGEMENT SYSTEM AND METHOD OF USING SAME

CROSS-REFERENCE TO RELATED APPLICATIONS

This application is a continuation-in-part patent application of U.S. patent application Ser. No. 09/358,355, filed Jul. 21, 1999, and entitled "ENTERPRISE HEALTHCARE MANAGEMENT SYSTEM AND METHOD OF USING SAME," which is a continuation-in-part patent application of U.S. patent application Ser. No. 08/977,522, filed Nov. 24, 1997, now U.S. Pat. No. 6,401,072 and entitled "CLINICAL CRITICAL CARE PATH SYSTEM AND METHOD OF USING SAME," which are incorporated herein by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Technical Field

The field of the present invention is healthcare management systems for healthcare enterprises. More specifically, the present invention relates to providing software applications for use by healthcare enterprises having a plurality of facilities.

2. Background Art

Modernly, primary healthcare is often times provided by healthcare enterprises. A healthcare enterprise is a group of healthcare facilities including, for example, hospitals, laboratories, pharmacies, and others. Healthcare enterprises can be expansive, encompassing hundreds of doctors and many geographically widely dispersed point of care facilities. Alternatively, they can be more modest in size having just a few facilities.

However, no matter what the size of the enterprise, all healthcare enterprises are coming under increased pressure to improve patient care without incurring undue additional expense. Indeed, successful healthcare enterprises must become more efficient and effective in providing patient services to remain viable. Thus, enterprises are striving to increase efficiency, while maintaining or improving patient care. For example, healthcare facilities are merging to form larger enterprises. In such a manner, the larger healthcare enterprises hope to improve efficiency through economy of scale.

Most healthcare enterprises have computer systems, and many have established local area networks within their facilities. The established computer systems typically perform a variety of particular and discrete functions. For example, a facility may have a clinical information system as described in U.S. patent application Ser. No. 08/977,522 for managing and presenting patient care management plans. The hospital may have other systems for financial and administrative functions. However, many of these established computer systems are unable to provide the information required to support healthcare enterprises in the modern managed care environment in an efficient and economical manner.

Further, each facility may have computer systems that operate differently and store information in diverse formats. Thus, information from different facilities of the same enterprise may not be readily usable by another facility within the same enterprise. For example, if a patient has been seen at two or more different facilities of an enterprise, the medical number assigned to the patient may be different for each facility. Therefore, associating a person with a complete medical record is not always readily conceivable, or in some cases even impossible using current known computerized healthcare systems.

Thus, the current computer, network, and application systems used by healthcare enterprises are incapable of providing sufficient uniform decision support with their existing computer facilities. Unfortunately, to remain viable, healthcare enterprises must upgrade their existing computer systems, and expand networks.

Such problems are made even more complex in the present merger environment. For example, merged facilities have existing medical information stored in incompatible formats. Planned economy of scale benefits can not be fully realized when data is not readily shareable between facilities. Further, healthcare practitioners from remote facilities now must have easy and efficient access to information on patients in other facilities, and even in other enterprises. For example, a practitioner requires an effective process for associating a patient with a medical file in an accurate and efficient manner. If such a positive identification can not be made, then proper medical treatment may be delayed, or worse, an incorrect treatment may be provided to the patient.

A healthcare enterprise having multiple facilities may encounter several problems when admitting a patient. For example, it would be helpful to know whether or not the patient to be admitted is a current patient or had been previously admitted at any of the facilities of the same enterprise. Since each of the facilities may be using record management features incompatible with the other facilities, there is no efficient manner to find if a patient had been previously admitted to the same enterprise.

Confidently identifying the to-be-admitted patient can be a daunting task. However, it is critical that the patient be positively associated with their true and complete medical record, if available. Such an identification task is exacerbated if the patient is unconscious. In such a manner, the person admitting the patient must rely solely on anecdotal information to establish the identity of the patient. Thus, the actual identity of the patient may not be established, or an incorrect identity made. Either way, providing treatment for the patient is difficult and may even result in harmful delays or treatment for the patient.

Once a patient has been successfully admitted to a multi-facility enterprise, then it is typical for several practitioners to become involved in providing healthcare to that patient. For example, doctors, nurses, laboratory technicians, radiologists, and pharmacists are needed to implement a successful treatment plan. However, these healthcare providers may be located in separate facilities, which may be widely dispersed geographically.

In providing healthcare to a patient, it is highly desirable that a complete medical history be available to healthcare practitioners. However, in the modern healthcare environment, patients routinely are transferred to different facilities of the same enterprise. Thus, over a period of years a patient's medical record becomes fragmented and dispersed among the various facilities of an enterprise.

Therefore, in general, it would be highly desirable to have a new computerized system for more efficiently and effectively communicating patient information among the various facilities of a healthcare enterprise.

The new system further needs to be quickly and confidently installed without burdensome expense to the enterprise. It is also desirable that existing legacy applications, computers, and networks cooperate with the new system. In such a manner the enterprise preserves prior information technology investments.

SUMMARY OF THE INVENTION

It is therefore an object of the present invention to provide a new enterprise healthcare management system for providing improved communication between healthcare facilities.

In another separate object of the present invention the new healthcare management system should enable a remote practitioner to easily access or modify a patient's complete chart.

Briefly, the above and further objects are realized by providing a new enterprise healthcare management system and method of using same. The enterprise healthcare management system and method includes a novel healthcare management system. The healthcare management system includes a server system connected to a plurality of enterprise facilities. A master index and a shared document repository on the server facilitate positively identifying patients and confidently associating that patient with proper medical records. The method of using the system also facilitates finding where in the enterprise a patient is located, and identifying available patient records. Healthcare practitioners also use the healthcare management system to access a patient treatment plan system, irrespective of which enterprise facility presently has the patient or which enterprise treatment plan system operates the patient treatment plan.

Advantageously, the new healthcare management system facilitates a healthcare enterprise's positively identifying patients and associating the identified patient with that patient's records. In such manner a patient can be admitted to an enterprise facility more efficiently. Further, as a patient moves to different locations and facilities within the enterprise, practitioners can confidently identify the patient prior to administering treatment. Therefore, the quality of delivered healthcare is improved.

The healthcare management system also enables a practitioner to quickly find where a patient is located in the enterprise, and determine what records exist and where the records can be found. By enabling such easy access to complete information, the healthcare management system allows the healthcare enterprise to operate more efficiently.

Further, the healthcare management system enables a practitioner at any enterprise facility to seamlessly use the treatment plan system for any enterprise patient. Thus, remote practitioners can efficiently access patient treatment plans so that the practitioner can review, adjust, and implement patient treatment plans.

The new healthcare management system also easily adjusts to changes within the enterprise. As the enterprise grows, adds facilities, sells facilities, and changes, the new system easily and cost effectively scales to facilitate the new level of need.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein.

BEST MODE FOR CARRYING OUT THE INVENTION

Figure 1:
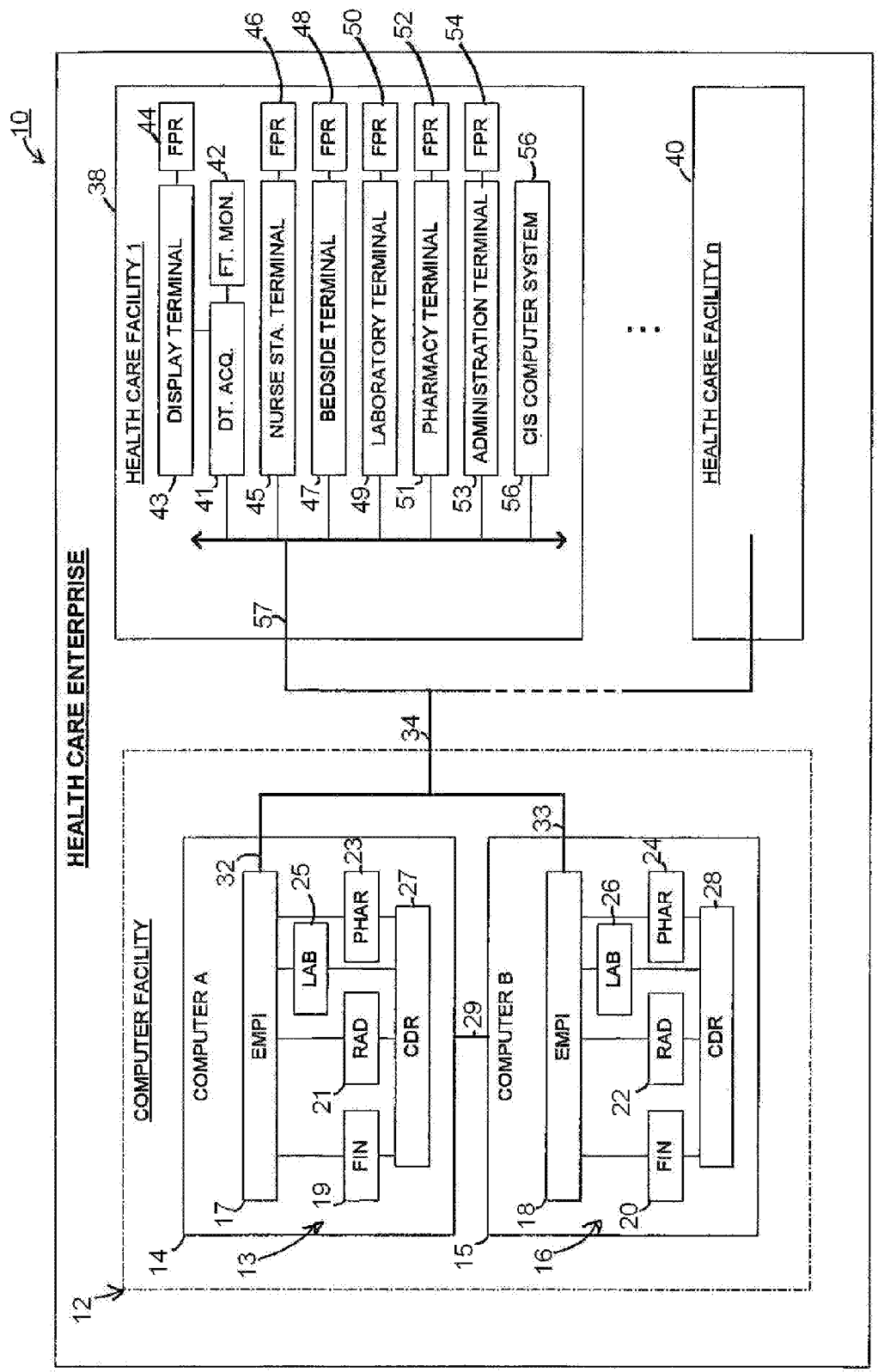
FIG. 1 is a block diagram showing a healthcare enterprise made in accordance with the present invention; and having multiple facilities.

Referring now to the drawings, and more particularly to FIG. 1 thereof, there is shown a new healthcare management system 10 which is constructed in accordance with the present invention. The healthcare management system 10 is for use in healthcare enterprises comprising two or more facilities. These facilities, for example, may provide a point of care for healthcare patients.

The healthcare management system 10 generally comprises a redundant server system 12 which is connected via a network 34 to the healthcare facilities 38 and 40. Thereby, healthcare practitioners in the healthcare facility, such as healthcare facility 38, access the server system 12 from terminals. Each healthcare facility may be operating its own clinical information system (CIS) computer system 56. The CIS system provides, for example, the implementation of treatment plans for patients, as more fully addressed in the patient applications. Although each facility has a separate CIS system, the server system 12 has an enterprise master patient index (EMPI) 17 and 18 for storing patient identifiers from all healthcare facilities. In such a manner, a health practitioner at any healthcare facility can find and retrieve information on any enterprise patient irrespective of which facility the patient is currently located.

In operation the server system 12 operates a suite of healthcare software applications 13 and 16 for providing software applications for the facilities of the healthcare enterprise. Associated with the suite of applications 13 and 16 is a common document repository (CDR) 27 and 28 for providing commonly accessible storage areas for all healthcare facilities. Further, the EMPI 17 and 18 store patient identifiers which are accessible at all enterprise facilities.

Additionally, the EMPI 17 and 18 may contain authorization information related to healthcare practitioners. For example, a nurse practitioner may approach nursing station terminal 45 and desire to view a particular patient's medical record. The nurse enters basic authorization information into the nurse's station terminal 45 which is received at the server system 12 and compare to authorization information within the EMPI. Provided the nurse initially appears to be a valid user, the nurse will be prompted to place his/her finger onto fingerprint reader 46. The fingerprint reader 46 scans the nurse's finger to record a fingerprint pattern. Information indicative of the fingerprint pattern is also sent to the server system 12 where it is compared to fingerprint pattern information stored in the EMPI. If the nurse is a valid user of the system, and has authorization proper for the requested action, the server system 12 allows the nurse to proceed with the desired action.

The nurse at nurse's station 45 may then enter patient specific information into the nurse's station terminal 45. The patient specific information is received at the server system 12 where the patient specific information is compared to the patient identifiers within the EMPI 17 and 18. If inconclusive patient specific information has been entered, the EMPI may identify several patients substantially matching the received patient's specific information. Thereby, the server system 12 retrieves further patient information for each identified possible match and forwards the more complete patient information back to the nurse's station terminal 45. The nurse then reviews the received more complete medical records and selects with confidence the medical record for the patient at issue. In such a manner the nurse positively identifies a patient and associates the patient to their true medical record file.

With the healthcare management system 10 generally described, component parts will now be discussed in more detail. The server system 12 is a redundant computer system having computer A 14 and computer B 15. Computer A 14 is connected to computer B 15 via redundant link 29. In such a manner, both computer A and computer B operate simultaneously to assure that each is running properly. If one of the computers fails, then the failing computer is shut down and the remaining redundant computer continues on, thereby providing service in an uninterrupted manner. The installation and use of redundant computer systems is well known in the art.

Both computer A 14 and computer B 15 operate a suite of healthcare applications 13 and 16. The suite may include financial software 19 and 20, radiology software 21 and 22, laboratory software 25 and 26, and pharmacy software 23 and 24. Although four applications are identified, those skilled in the art will recognize other applications may be substituted or supplemented. Each of computer 14 and 15 has a CDR data base 27 and 28 for storing information in a manner such that the information can be shared between suite applications. In such a manner, multi-disciplinary information may be retrieved from the CDR 27 and 28. Further, the CDR 27 and 28 contains information received from applications operating at the healthcare facilities 38 and 40. For example, healthcare facility 1 38 has a computer system operating a CIS system 56. Patient care information from CIS computer system 56 is sent to server system 12 where it is stored on the CDR 27 and 28. In such a manner, healthcare practitioners at any healthcare facility 38 and 40 can retrieve and review documents stored on the CDR relating to the CIS computer system 56.

Both computer A 14 and computer B 15 have an EMPI file. The EMPI file is the master index for accessing the server system 12 and finding patients and patient information. The patient identifier information include identifying characteristics for identifying patients with a high degree of certainty. Such patient identifiers may include name, birth date, social security number, birth date, gender, fingerprint pattern data, or race. Those skilled in the art will recognize other identifiers may be used. The EMPI thereby stores patient identifiers for all patients of the healthcare enterprise. Thus, irrespective of which facility admits a patient, patient information is stored in a common and accessible format. Subsequently, information related to that patient can then be found and retrieved by any healthcare practitioner from any healthcare facility within the enterprise. Indeed, one of the healthcare identifiers even tracks the present location for an admitted patient.

Computer A 17 accesses the network 34 at access point 32 and computer B 15 accesses the network 34 at access point 33. As shown, access to the server system is controlled by the EMPI. In such a manner, EMPI identifies those healthcare practitioners authorized to access features of the server system 12 and the practitioner's authorization level. For example, some healthcare practitioners may not be able to access the server system 12 at all, while others may have an ability to review patient medical records, but not financial records, and others may have full rights to all data. Thus, the EMPI tracks who can validly access the system at what authorization level.

To further increase security on the system, the EMPI may also store fingerprint information for each authorized user. In such a manner, during initialization of the system each authorized user has their fingerprints scanned and stored in the EMPI. Then at a later time when the practitioner desires to access the system, the practitioner uses a remote fingerprint reader such as remote fingerprint reader 46 to scan their fingerprint. The scanned fingerprint is compared with the stored fingerprint information in the server system 12. In such a manner, the server system 12 can verify with a high degree of confidence that the practitioner can be trusted.

Each healthcare enterprise generally has more than one facility. For example, the healthcare enterprise of FIG. 1 has n healthcare facilities 40. Each of the healthcare facilities will be similar to healthcare facility 1, although some facilities may have more, less, or a different mix of functions as compared to healthcare facility 1 38.

Healthcare facility 1 38 is a hospital for providing a point of care for patients. In such a manner the healthcare facility 38 has specialized equipment such as data acquisition device 41 and fetal monitor 42 for monitoring newborn babies. Associated with the data acquisition device 41 may be a display terminal 43 whereby a healthcare practitioner monitors the data acquisition unit 41 and gains access to the entire computer system, including the server system 12. Specifically, the practitioner at display terminal 43 may need to access the CIS computer system 56 to review or update a treatment plan for the infant on the fetal monitor 42.

However, the CIS computer system for the newborn may be operating at a different facility. For example, the newborn baby on fetal monitor 43 may have been originally admitted to an emergency facility where the emergency facility's CIS was used to establish a treatment plan. As the newborn progressed, he/she may have been moved to facility 1 38, which is remote from the emergency facility. Thus, when the practitioner needs to access, review, and update the CIS treatment plan for the newborn, the practitioner does not access CIS computer system 56, but must access the CIS computer system for the emergency facility. Such access, as will be further discussed, is provided by display terminal 43.

Attached to display terminal 43 is a fingerprint reader 44 for verifying the practitioner and assuring the practitioner has the necessary authorization to perform the desired function. The fingerprint reader can also be used to assist in positively identifying patients through fingerprint matching. Healthcare facility 38 also has a plurality of nurse's stations with terminals such as nurse's station terminal 45. Each nurse's station terminal has a fingerprint reader 46, again for providing verifications. Bedside terminals 47 may be positioned adjacent patients so that clinical records can be reviewed and updated adjacent patient location. Bedside terminal 47 has fingerprint reader 48 connected thereto for patient identification and practitioner authorization.

Major healthcare facilities also have a laboratory and a pharmacy associated therewith. Therefore, the laboratory will have a laboratory 49 with fingerprint reader 50 and the pharmacy will have a pharmacy terminal 51 with a fingerprint reader 52. In such a manner, laboratory personnel and pharmacy personnel have full access to the CIS computer system 56 and the server system 12. Healthcare facilities also have administration functions for financial, insurance, and admitting purposes. For example, administration terminal 53 has fingerprint reading 54 connected thereto and may be used for admitting patients.

The various terminals and computers within healthcare facility 38 may be interconnected by a network 57. Indeed, network 57 can even be a complete Internet system. The network 57 connects to the server system 12 via network 34.

Other healthcare facilities such as healthcare facility n 40 are part of the healthcare enterprise. Several of these healthcare facilities may have their own CIS computer system operating. These CIS computer systems may be installed and running locally at the healthcare facility such as shown in healthcare facility 38, or the CIS system may be operating remotely on the server system 12 (not shown).

Figure 3:
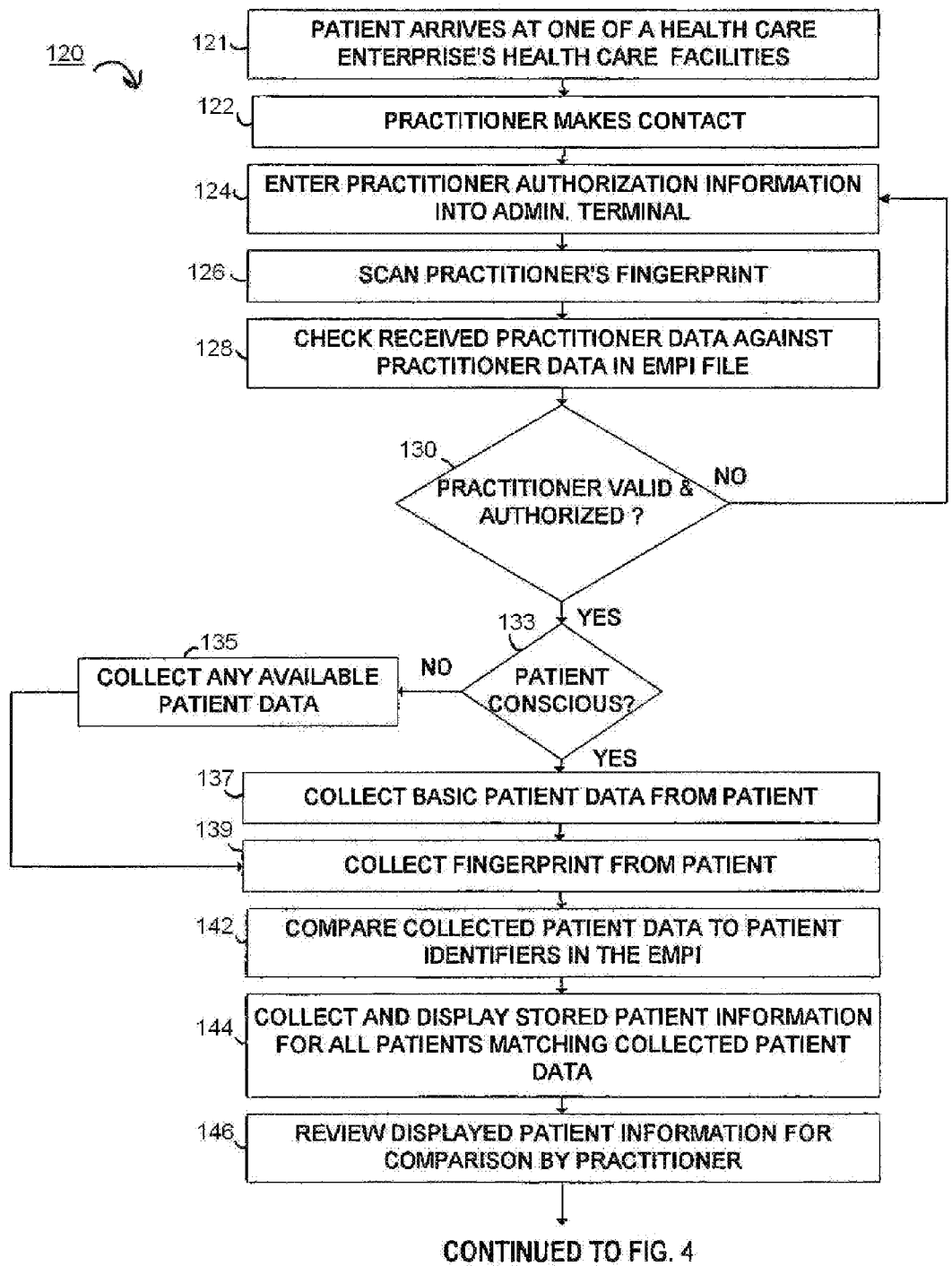
FIG. 3 is a flowchart of a method enterprise in accordance with the present invention for admitting a patient to a healthcare.
Figure 4:
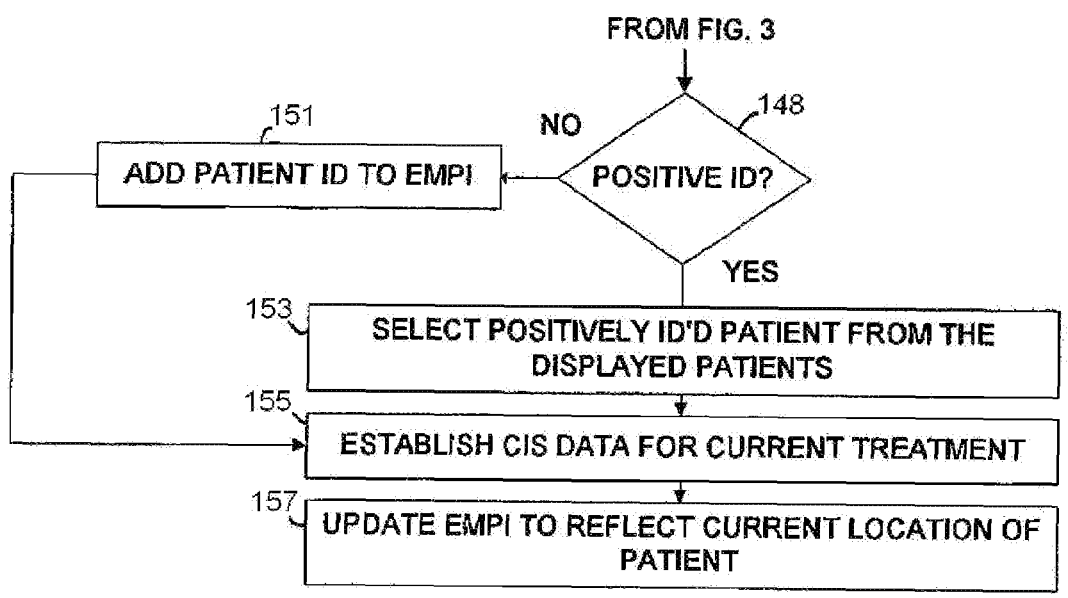
FIG. 4 is a continuation flowchart of FIG. 3.

Referring now to FIG. 3 there is shown a method of admitting a patient 120 using the healthcare management system 10 of FIG. 1. As shown in block 121, a patient arrives at one of the healthcare facilities for the healthcare enterprise. A practitioner makes contact in block 122. This contact typically will be by a practitioner entering admitting information into an administrative terminal such as administrative terminal 53 or by an emergency room personnel admitting information into an emergency room terminal (not shown). The practitioner enters authorization information, such as the practitioner's user name and password into a terminal such as administration terminal 53 as shown in block 124. Other information may be required, such as a challenge security system for further verifying the practitioner.

During the verification process, the practitioner is directed to place his/her finger on a fingerprint reader and the fingerprint reader scans the practitioner's fingerprint as shown in block 126. The use of a fingerprint reader adds significant additional security to the system, but is optionally used. Further, those skilled in the art will recognize other types of security devices may be added. For example, speech patterns and retina scans can also be used for verifying and identifying people.

Referring again to FIG. 3, block 128 shows that the information indicative of the scanned practitioner's fingerprint is compared to the practitioner fingerprint information stored in the EMPI file. In block 130, if the practitioner fails the authorization routine, then the practitioner must reenter or correct the information. Those skilled in the art will recognize that often a user is given a set number of attempts, such as three attempts, before the system generates an intrusion alert. The practitioner also must be authorized to perform the particular function requested. Here, the practitioner desires to admit a patient. Each practitioner has an authorization level associated therewith which determines what functions they may properly perform in the system. If the practitioner is valid and authorized, then the patient be properly admitted by that practitioner.

The practitioner then determines if the patient is conscious in block 133. If not conscious, the practitioner collects any available information from other parties such as family members, emergency personnel, or documents retrieved from the patient's body as shown in block 135. If the patient is conscious, then the practitioner can interrogate the patient for basic patient information as shown in block 137. For example, the practitioner will collect patient name, age, birth date, social security, and other data that can positively identify the patient. Block 139 shows that optionally the fingerprint reader can be used to collect a fingerprint scan from the patient. This can be the same fingerprint reader used by the practitioner for verification and authorization. In such a manner, the scanned patient fingerprint is compared to stored fingerprint information in the EMPI as shown in block 142. Such a fingerprint scan comparison facilities correctly identifying a patient.

The data collected by the practitioner, and the fingerprint scan information, if collected, may not positively identify the patient. Therefore, there may be multiple patients which sufficiently match the collected data that the system cannot automatically make a positive determination based on the collected patient information. Therefore, block 144 shows that the system collects and displays stored patient information for all patients matching the collected patient data. These tentative patients have identifiers sufficiently close to the collected patient data that the practitioner will need to review the additional patient information to determine which patient is actually waiting to be admitted as shown in block 146. This additional patient information can include demographic information such as address, and medical record data. Those skilled in the art recognize other information can be included as additional patient information.

Even though the additional patient information has possibly been collected at multiple enterprise facilities by different CIS computer systems, since each facility's CIS system forwards information to the CDR, the CDR has substantial patient information for the whole enterprise. In such a manner the additional patient information for all tentative patients is quickly and efficiently sent to the practitioner.

After reviewing the additional patient information, if the patient cannot be positively identified, then the practitioner adds the patient to the EMPI as a new patient as indicated in block 151. In such a manner, collected basic patient specific information and the fingerprint scan will be stored in the EMPI for future use. The practitioner then can proceed to establish a CIS treatment plan for the newly added patient as shown in block 155. However, if the practitioner is able to make a positive ID of the patient, then the practitioner selects the positively identified patient from the list of tentative patients as shown in block 153. The practitioner then can proceed to review and use the CIS system to establish the current treatment plan as shown in block 155. Finally, the EMPI file is updated to reflect that the patient has been admitted and is located at the current facility location.

Figure 5:
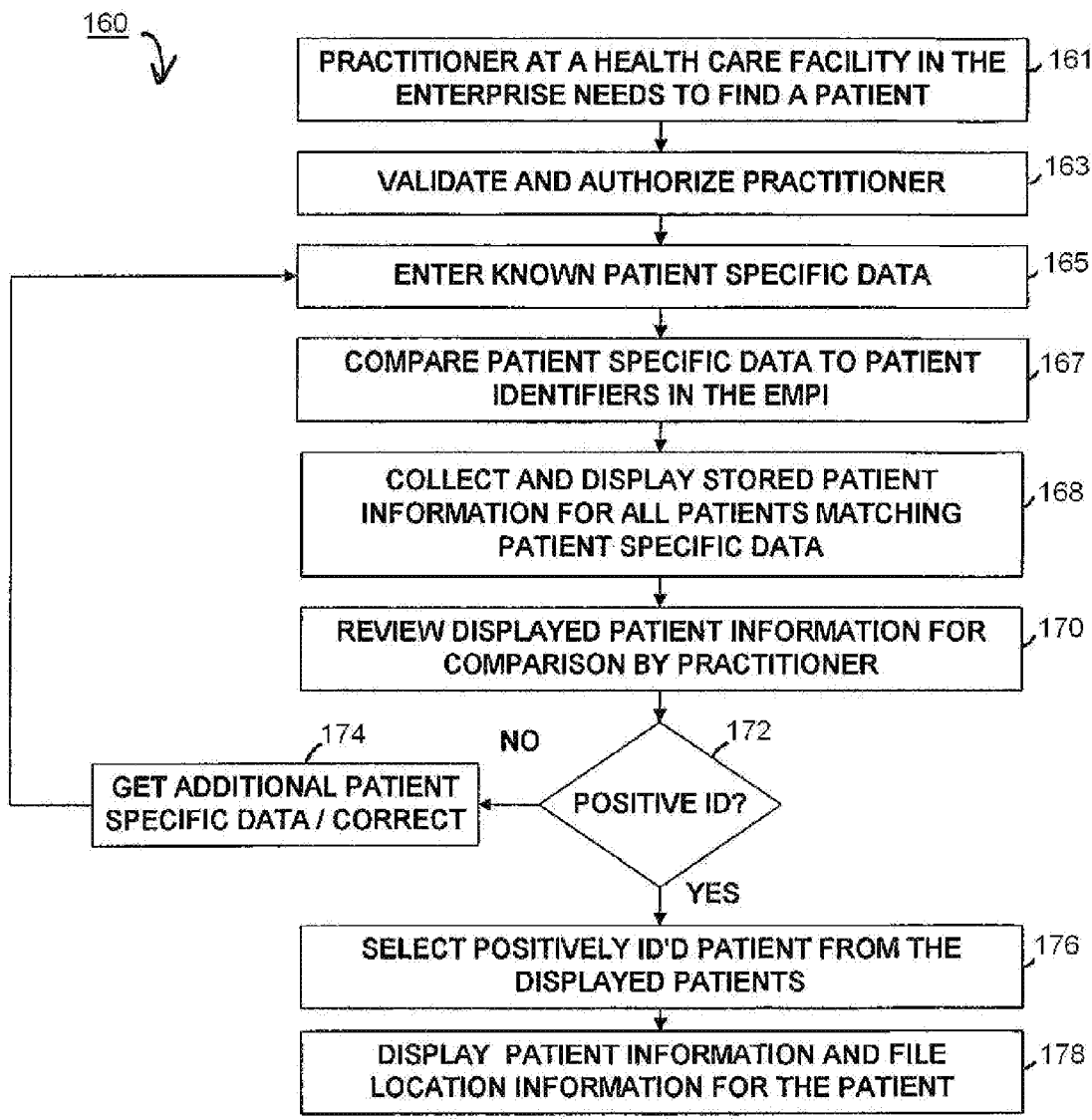
FIG. 5 is a flowchart of a method in accordance with the present invention for finding a patient at a healthcare enterprise.

Referring now to FIG. 5, there is shown a method for finding a patient using the healthcare management system of FIG. 1. FIG. 5 shows in block 161 that a practitioner at a healthcare facility needs to find a patient. The practitioner may believe the person is a currently admitted patient, or may want to get an updated status on an old patient. The practitioner can be located in the same or a different facility from where the patient is located. Indeed, the practitioner may not even know in what facility the patient is presently located.

As described in detail above, the practitioner is verified and authorized as shown in block 163. In block 165, the practitioner enters patient specific data relating to the patient at issue. As described more fully above, the system compares the patient specific data to patient identifier data in the EMPI in block 167 and then collects and displays tentative patients in block 167. The practitioner then can review the tentative patient list in block 170 and select, if displayed, the positively identified patient as shown in blocks 172 and 176. If no such patient can be positively identified, the practitioner is instructed to enter additional patient data as shown in block 174. However, since the practitioner is attempting to find information on a patient they believe to be admitted or an old patient, the practitioner is likely to have very specific patient identification information such as a patient medical number. In such a manner, the patient identification steps can be abbreviated as the practitioner already has positive ID information on the patient at issue.

The practitioner selects the positively identified patient at issue in block 176. Block 178 shows that the system then displays the identified patient information. Patient information can be included such information as the location information for the patient at issue. Further, the system can show any available patient records and where those records are located. Thereby, the practitioner can quickly locate not only the patient at issue, but all related medical and CIS records for that patient.

At other times the practitioner may desire to access the patient's CIS system to review and update the patient's treatment plan. As briefly discussed earlier, the patient's treatment plan may be on a CIS system at a different facility than where the patient is presently located. Further, the CIS system may be different from the CIS system where the practitioner resides. For example, an enterprise may have several facilities, with each facility operating an associated CIS system. Since the patient may be at a facility remote from the practitioner, the practitioner's local CIS system has no visibility to the patient's CIS files.

Figure 6:
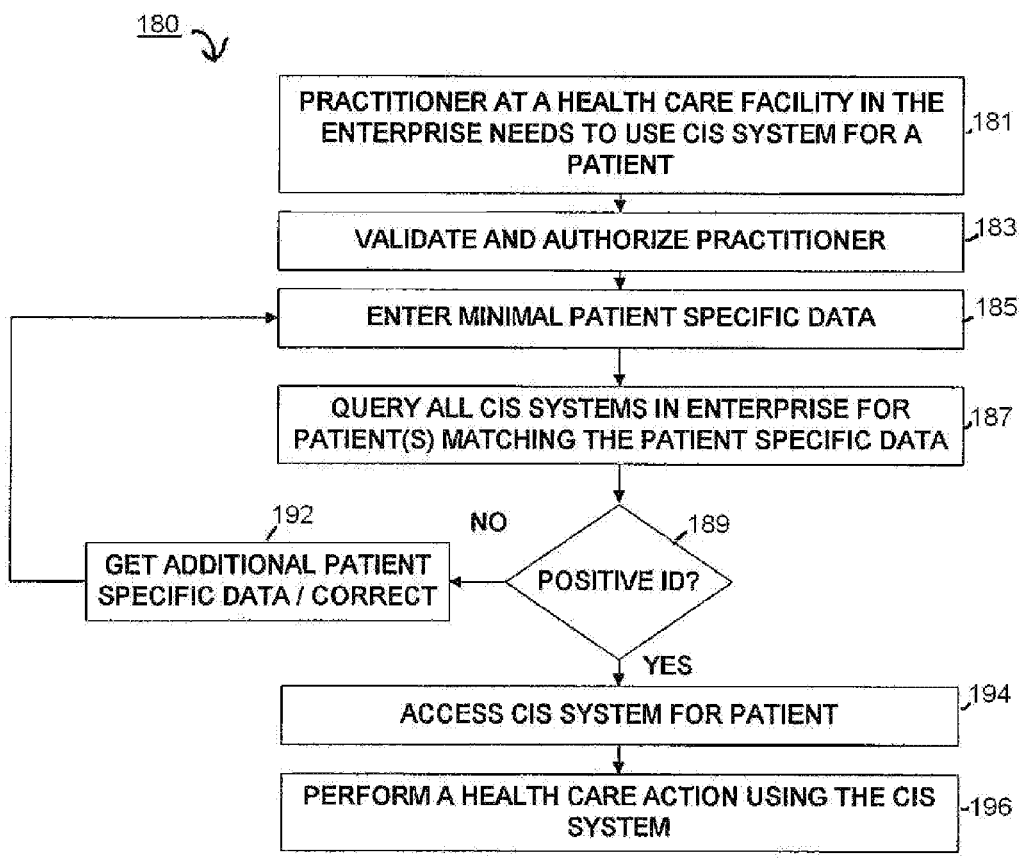
FIG. 6 is a flowchart of a method in accordance with the present invention for accessing a CIS system for a patient.

Referring now to FIG. 6 there is shown a method 180 for a practitioner to access the CIS system for any patient in the enterprise. Block 181 shows that the practitioner knows a patient is within the enterprise system and that the practitioner wants to review and adjust the treatment plan for that patient. For example, a remotely located specialist may want to review a patient's medical file and make adjustments to the treatment plan. After validating and authorizing as shown in block 183 and discussed fully above, the practitioner enters minimal patient specific data into a terminal as shown in block 185. For example, the practitioner may simply enter the name of the patient or the patient medical ID number. The patient identification process is simplified as the practitioner is confident the patient is presently under care and is already somewhat familiar with the specifics of the patient's case. Thus, the risk of mis-identification is minimized.

The system then queries, in parallel, all CIS systems in the enterprise for patient(s) matching the entered patient specific data as shown in lock 187. If no matching patients are found, then block 192 asks the practitioner for additional information. If a positive ID is found in block 189, then the method accesses the CIS system having the patient's treatment plan as shown in block 194. In such a manner, the practitioner accesses a patient's CIS system by simply entering simple ID data irrespective of what facility is operating the CIS system for that patient.

Figure 2:
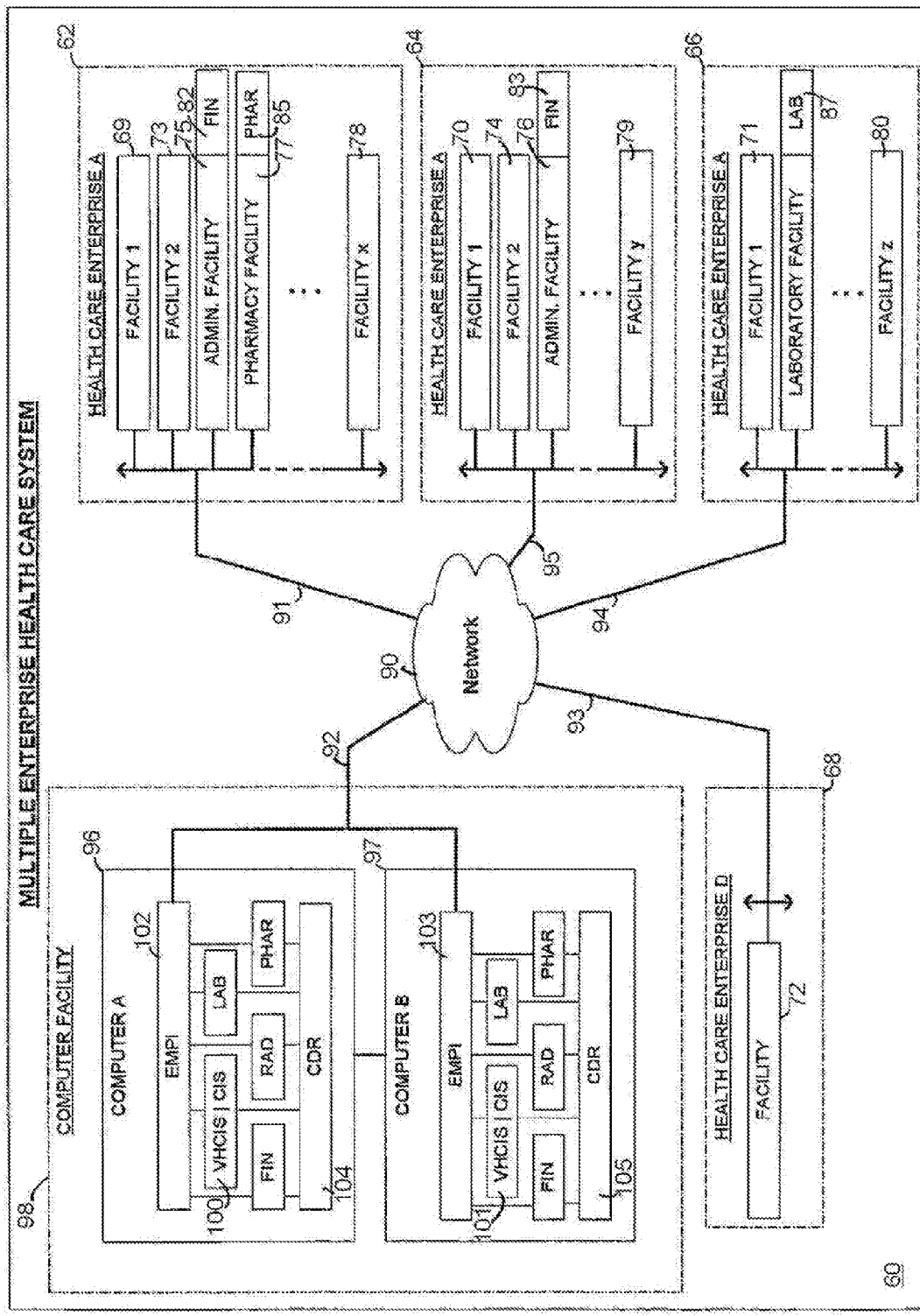
FIG. 2 is a block diagram of a multiple enterprise healthcare system made in accordance with the present invention showing the interconnection of a plurality of healthcare enterprises.

Referring now to FIG. 2 there is shown another healthcare management system made in accordance with the present invention. This multiple enterprise healthcare system 60 not only provides healthcare management tools for the individual enterprise, but enables a sharing of selected information between healthcare enterprises. In such a manner, healthcare may be delivered to a patient in an expedient and efficient manner irrespective of which healthcare facility or healthcare enterprise the patient selects.

The multiple enterprise healthcare system 10 comprises multiple healthcare enterprises such as healthcare enterprises 62, 64, 66 and 68. For example, healthcare enterprise 62 is similar to the healthcare enterprise described in FIG. 1. In such a manner, healthcare enterprise 62 comprises multiple facilities such as facility 1, 69, facility 2, 73, an administration facility 75, a pharmacy facility 77 and other unspecified facilities up to facility x, 78. Healthcare enterprise 62 has financial application solutions 82 operating at its administration facility 75 and pharmacy support software 85 active at its pharmacy facility 77. In such a manner, healthcare enterprise 62 is self sufficient for financial and pharmacy software and therefore will not need to utilize the financial and pharmacy services available from the central server 98. However, information from the financial 82 and pharmacy 85 software will be sent to the CDR 104 and 105 of the server system 98 to facilitate multi-disciplinary decision support.

Healthcare enterprise 64 is, similar to healthcare enterprise 62 and has facility 1 70, facility 2 74 and administration facility 76 operating financial software 83 and other facilities up to facility y 79. However, healthcare facility 64 does not have any pharmacy facility. Healthcare enterprise 66 is also similar to healthcare enterprises 62 and 64 except that this enterprise operates on a slightly smaller scale. In such a manner, healthcare enterprise 66 has a facility 1 72, a laboratory facility operating lab software 87, and up to a facility z 80. Finally, healthcare enterprise D has only a single facility 72.

Each healthcare enterprise can supplement local healthcare applications by using remotely hosted applications on the server. For example, healthcare facility 1 is not locally operating any laboratory control application. Therefore, healthcare facility 1 may operate remotely the laboratory software operating on the server system 98. In such a manner enterprises may supplement existing capability by simply remotely hosting applications from the server system 98.

None of the healthcare enterprises 62, 64, 66, or 68 are presently running a local facility CIS system. Each of the healthcare enterprises connects to a network 90 via a network connection such as network connection 91, 93, 94 or 95. The network 90 may be any one of several available public or private networks, such as the Internet. For public networks, additional security becomes necessary. The network 90 connects to the computer server 98 via link 92.

Computer server 98 is similar to server system 12 discussed above and comprises network computers 96 and 98. Server system 98 operates the same suite of healthcare applications as operating on server system 12, except server system 98 has an additional VHCIS/CIS application 100 and 101. This application is for providing CIS functionality for each healthcare facility not having a local facility CIS system. As with server system 12, the EMPI 102 and 103 provide practitioner authorization and patient finding functions.

When installing the multiple enterprise healthcare system, each healthcare enterprise must select how that enterprise will implement CIS systems. For example, the healthcare enterprise can choose to operate CIS on a facility by facility basis. For example, if healthcare enterprise 62 selects to operate CIS on a facility-by-facility basis, facility 1 will have a CIS system which operates separately from the CIS facility for facility 2. To make such a selection, the healthcare enterprise 62 chooses to install CIS in blocks 100 and 101.

In making such a selection, the server system 98 establishes a physically or logically partitioned data base for each facility of the healthcare enterprise. In such a manner, the CIS for each facility operates independent of every other facility. Of course, using the inventive aspects already discussed, practitioners at facility 1 69, for example, can find patient information and access the CIS system for facility 2 73.

However, an enterprise may choose to operate its CIS system on a enterprise wide basis. In such a manner, all facilities in the enterprise operate on the same CIS system. To make such an election, the healthcare enterprise desiring to operate CIS on an enterprise wide basis selects to install VHCIS (virtual hospital clinical information system) in block 100 and 101. If the VHCIS is installed, then the server system 98 establishes a data base for holding all CIS information for all facilities.

Figure 7:
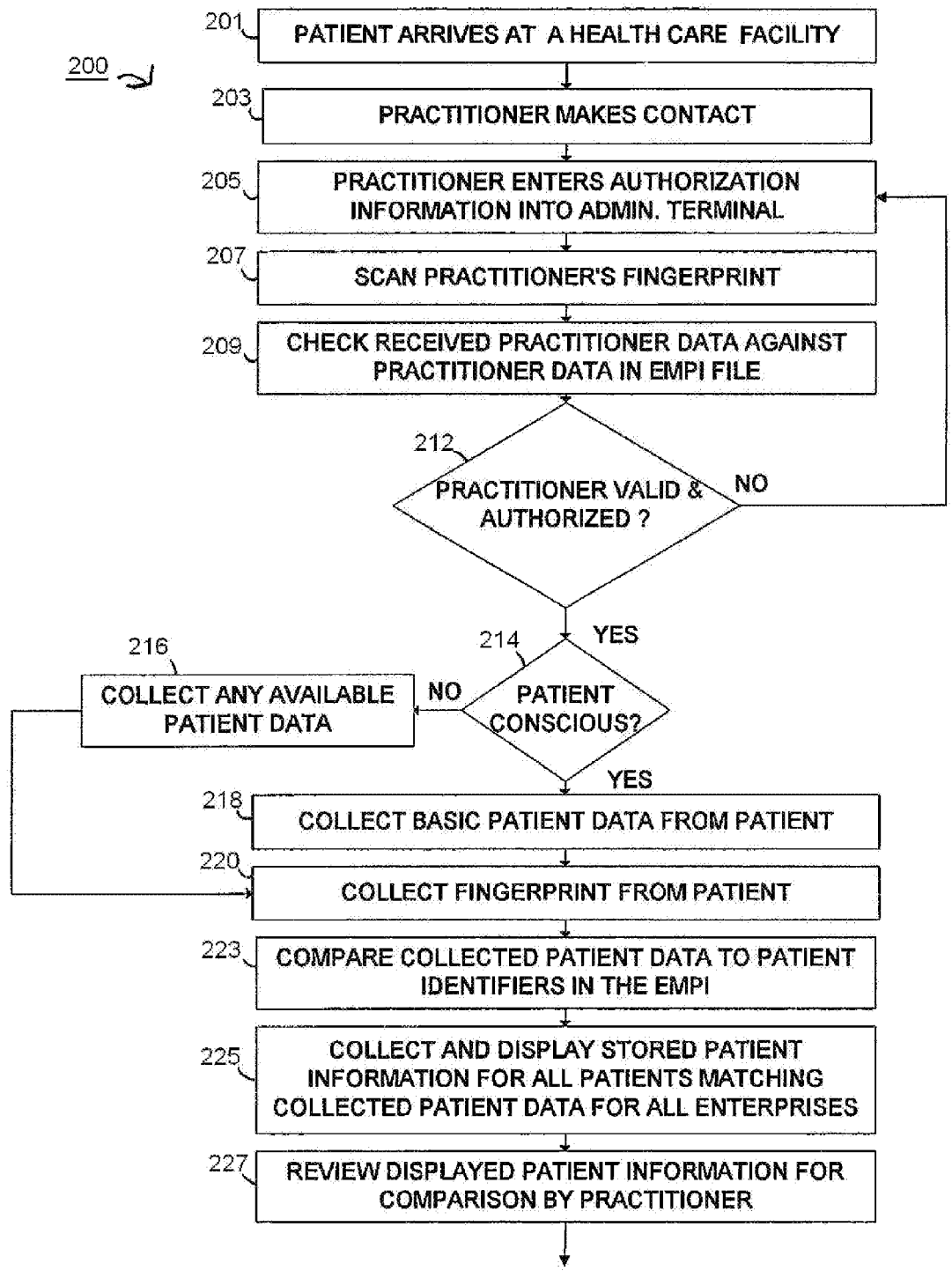
FIG. 7 is a flowchart of a method in accordance with the present invention for admitting a patient into a healthcare facility.

Referring now to FIG. 7 there is shown a method of admitting a patient into the multiple enterprise healthcare system as shown in FIG. 2. The method of admitting 200 is similar to method of admitting 120 except the method operates on a network connecting multiple enterprises. In method 200 a patient arrives at a healthcare facility for any enterprise as shown in block 201. The practitioner performs an authorization routine in blocks 203, 205, 207, 209, and 212 similar to the authorization routines discussed in FIG. 3.

Provided the practitioner is valid and authorized as shown in block 212, then the practitioner proceeds to collect information from the patient in blocks 214, 216, 218 and 220 in a manner similar to that shown in FIG. 3. The collected patient data is compared to the patient identifiers stored in the EMPI in block 223. The EMPI file contains not only patient identifiers for the practitioner's enterprise, but includes patient identifiers from the other networked healthcare enterprises. In such a manner, block 225 shows that tentative patient are selected from all enterprises and displayed for the review of the practitioner in block 227. Thereby, the practitioner not only has visibility to patients of the practitioner's enterprise, but searches other network enterprises for other possible matches. Of course, those skilled in the art will recognize that healthcare information can only be shared between healthcare enterprises pursuant to proper legal authorization for the transfer. Thus, medical data is only transferred when necessary approvals have been received.

Figure 8:
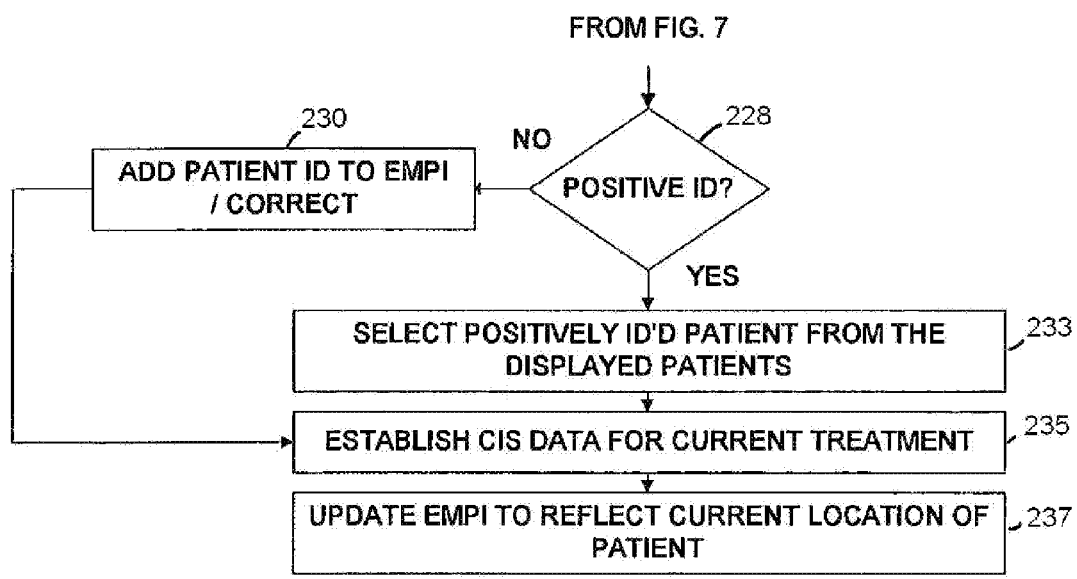
FIG. 8 is a continuation flowchart of FIG. 7.

Referring now to FIG. 8, the practitioner selects the positively identified patient in blocks 228 and 233, if displayed. The practitioner adds the patient to the EMPI as a new patient in block 230 if not positively identified. Subsequently, the practitioner can establish CIS data for current treatment of the patient as shown in block 235. Finally, the EMPI file is updated to reflect that the patient is currently admitted into a particular facility location.

Figure 9:
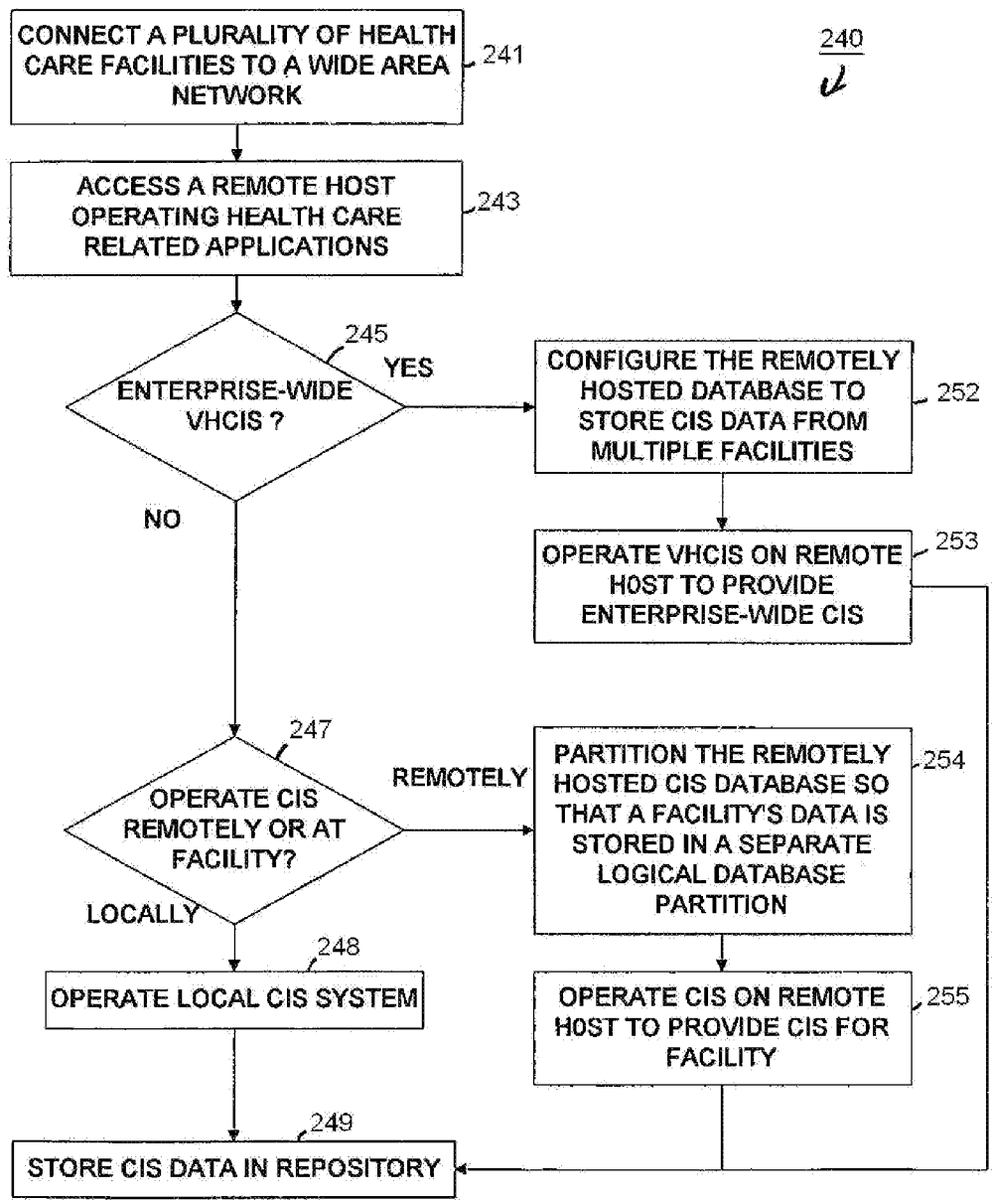
FIG. 9 is a flowchart of a method in accordance to the present invention for installing a healthcare facility management system.

Referring now to FIG. 9, there is shown a method of installing the multiple enterprise health system as shown in FIG. 2. Block 241 shows that a plurality of healthcare facilities are connected to a wide area network. Such facilities may be interconnected by an intranet which is then connected to the wide area network, or each facility may have its own connection into the wide area network.

A remote host operates healthcare related applications and each facility is given access to these applications as shown in block 243.

The enterprise must decide if they choose to operate CIS on an enterprise wide basis as shown in block 245. If the enterprise chooses to install the enterprise wide VHCIS, then block 252 shows that the remotely hosted data base stores CIS data from multiple facilities. As shown on block 253, the VHCIS operates on the remote host, providing CIS services for all facilities.

If the enterprise chooses not to operate enterprise wide CIS, then the enterprise must choose whether they will operate CIS remotely from a computer such as server system 98 or if they will operate CIS locally at each facility. In block 247, if the enterprise chooses to operate CIS remotely, then the remotely host data base is partitioned so that each facility's data is stored in a separate partition of the data base as shown in block 254. For that facility, as indicated in block 255, CIS then operates on the remote host computer system.

However, if the enterprise chooses to locally operate CIS at a facility, then CIS system is installed locally at the facility, as shown in block 248. However, CIS data from the local CIS system is still sent. However, to a repository at the remote host as shown in block 249. Thereby, whether the CIS is operated remotely or locally, the server system 98 stores CIS information for the enterprise. The enterprise may even choose to operate some facilities remotely and some facilities with local CIS.

Alternatively, an enterprise can elect to operate a subset of facilities using VHCIS, with other facilities operating either remote or local CIS systems. For example, an enterprise may operate all its general hospitals under a single VHCIS, but operate its specialty hospitals, such as a children's hospital, as a separate CIS. In such a manner the general hospitals would be active as VHCIS facilities, while the children's hospital would have a separate local or remote CIS system. Therefore, both CIS and VHCIS would be installed.

Although the preferred embodiment shows the CDR hosted on the server system, the CDR and/or the master index may also be distributed, such as on the local CIS systems.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method of accurately associating medical information with a given person in a healthcare enterprise, the enterprise having a plurality of healthcare facilities, comprising:

networking a centralized server system with at least one computer at each of the plurality of healthcare facilities, the centralized server system operating a suite of health care software applications;

generating a master index of enterprise patient names and their associated patient identifiers;

storing the master index on the centralized server system;

permitting access to the master index directly by practitioners at each of the plurality of healthcare facilities;

establishing in the centralized server system a shared document repository;

storing enterprise patient medical records in the shared document repository;

permitting access to the shared document repository to practitioners at each of the plurality of healthcare facilities;

receiving patient specific data regarding a certain person to be treated at one of the healthcare facilities;

comparing the patient specific data to the stored patient identifiers;

determining whether the comparing the patient specific data to the stored patient identifiers results in positively identifying the certain person;

determining a set of two or more tentative patients whose patient identifiers most closely correlate to the patient specific data, if the comparing the patient specific data to the stored patient identifiers results in identifying multiple patients;

displaying the set of tentative patients and their associated patient identifiers to facilitate a positive identification of the certain person;

enabling the practitioner to attempt to positively identify the certain person from the displayed patient identifiers in the displayed set of tentative patients;

receiving additional patient specific data regarding the certain person in response to an inability to positively identify the certain person from the displayed set of tentative patients;

comparing the patient specific data and the additional patient specific data to the stored patient identifiers;

determining whether the comparing the patient specific data and the additional patient specific data to the stored patient identifiers results in positively identifying the certain person;

determining another set of two or more tentative patients whose patient identifiers most closely correlate to the patient specific data and the additional patient specific data, if the comparing the patient specific data and the additional patient specific data to the stored patient identifiers results in identifying multiple patients;

displaying the another set of tentative patients and their associated patient identifiers to facilitate a positive identification of the certain person;

enabling the practitioner to attempt to positively identify the certain person from the displayed patient identifiers in the displayed another set of tentative patients;

permitting access, in response to the certain person being positively identified, directly to the shared document repository on the centralized server system storing the medical record for the certain person being positively identified; and adding the certain person to the master index as a new patient, in response to the certain person not being positively identified.

2. The method of claim 1, further comprising arranging said shared document repository as a partitioned data base, partitioning the data base among the plurality of facilities for the patient records associated with corresponding facilities.

3. The method of claim 1, further comprising selecting which of the plurality of facilities to operate a unified treatment plan system.

4. The method of claim 3, further comprising installing a treatment plan system on the centralized server system for a facility not selected to operate the unified treatment plan system.

5. The method of claim 3, further comprising installing a local treatment plan system at a facility not selected to operate the unified treatment plan system.

6. The method of claim 1, further comprising installing a unified treatment plan system on the centralized server system for each of the plurality of facilities.

7. The method of claim 1, wherein patient identifiers include fingerprint information.

8. The method of claim 1, wherein patent identifiers include demographic information.

9. The method of claim 1, further comprising verifying the identity of the practitioner.

10. The method of claim 1, further comprising verifying the identity of the practitioner using fingerprint information.

11. A system of accurately associating medical information with a given person in a healthcare enterprise, the enterprise having a plurality of healthcare facilities, comprising:

a centralized server system coupled by a network to at least one computer at each of the plurality of healthcare facilities, the centralized server system operating a suite of health care software applications;

means for generating a master index of enterprise patient names and their associated patient identifiers;

means for storing the master index on the centralized server system;

means for permitting access to the master index directly by practitioners at each of the plurality of healthcare facilities;

means for establishing in the centralized server system a shared document repository;

means for storing enterprise patient medical records in the shared document repository;

means for permitting access to the shared document repository to practitioners at each of the plurality of healthcare facilities;

means for receiving patient specific data regarding a certain person to be treated at one of the healthcare facilities;

means for comparing the patient specific data to the stored patient identifiers;

means for determining whether the means for comparing the patient specific data to the stored patient identifiers positively identifies the certain person;

means of determining a set of two or more tentative patients whose patient identifiers most closely correlate to the patient specific data, if the means for comparing the patient specific data to the stored patient identifiers results in identifying multiple patients;

means for displaying the set of tentative patients and their associated patient identifiers to facilitate a positive identification of the certain person;

means for enabling the practitioner to attempt to positively identify the certain person from the displayed patient identifiers in the displayed set of tentative patients;

means for receiving additional patient specific, data regarding the certain person in response to an inability to positively identify the certain person from the set of tentative patients;

means for comparing the patient specific data and the additional patient specific data to the stored patient identifiers;

means for determining whether the means for comparing the patient specific, data and the additional patient specific data to the stored patient identifiers positively identifies the certain person;

means for determining another set of two or more tentative patients whose patient identifiers most closely correlate to the patient specific data and the additional patient specific data, if the means for comparing the patient specific data and the additional patient specific data to the stored patient identifiers results in identifying multiple patients;

means for displaying the another set of tentative patients and their associated patient identifiers to facilitate a positive identification of the certain person;

means for enabling the practitioner to attempt to positively identify the certain person from the displayed patient identifiers in the displayed another set of tentative patients;

means for permitting access, in response to the certain person being positively identified, directly to the shared document repository on the centralized server system storing the medical record for the certain person being positively identified; and means for adding the certain person to the master index as a new patient, in response to the certain person not being positively identified.

12. The system of claim 11, further comprising means for arranging said shared document repository as a partitioned data base; means for partitioning the data base among the plurality of facilities for the patient records associated with corresponding facilities.

13. The system of claim 11, further comprising means for selecting which of the plurality of facilities to operate a unified treatment plan system.

14. The system of claim 13, further comprising means for installing a treatment plan system on the server for a facility not selected to operate the unified treatment plan system.

15. The system of claim 13, further comprising means for installing a local treatment plan system at a facility not selected to operate the unified treatment plan system.

16. The system of claim 11, further comprising means for installing a unified treatment plan system on the server for each of the plurality of facilities.

17. The system of claim 11, wherein patient identifiers include fingerprint information.

18. The system of claim 11, wherein patent identifiers include demographic information.

19. The system of claim 11, further comprising means for verifying the identity of the practitioner.

20. The system of claim 11, further comprising means for verifying the identity of the practitioner using fingerprint information.

21. A system of accurately associating medical information with a given person in a healthcare enterprise, the enterprise having a plurality of healthcare facilities, comprising:
   a centralized server system coupled by a network to at least one computer at each of the plurality of healthcare facilities, the centralized server system operating a suite of health care software applications;
   a first module for generating a master index of enterprise patient names and their associated patient identifiers;
   a second module for storing the master index on the centralized server system;
   a third module for permitting access to the master index directly by practitioners at each of the plurality of healthcare facilities;
   a fourth module for establishing in the centralized server system a shared document repository;
   a fifth module for permitting access to the shared repository to practitioners at each of the plurality of healthcare facilities;
   a sixth module for receiving patient specific data regarding a certain person to be treated at one of the healthcare facilities;
   a seventh module for comparing the specific data to the stored patient identifiers;
   an eighth module for determining whether the seventh module for comparing the patient specific data to the stored patient identifiers positively identifies the certain person;
   a ninth module for determining a set of two or more tentative patients whose patient identifiers most closely correlate to the patient specific data, if the seventh module for comparing the patient specific data and the additional patient specific data to the stored patient identifiers identifies multiple patients;
   a tenth module for displaying the set of tentative patients and their associated patient identifiers to facilitate a positive identification of the certain person;
   an eleventh module for enabling the practitioner to positively identify the certain person from the displayed patient identifiers in the displayed set of tentative patients;
   a twelfth module for receiving additional patient specific data regarding the certain person in response to an inability to positively identify the certain person from the set of tentative patients;
   a thirteenth module for comparing the patient specific data and the additional patient specific data to the stored patient identifiers;
   a fourteenth module for determining whether the thirteenth module for comparing the patient specific data and the additional patient specific data to the stored patient identifiers positively identifies the certain person;
   a fifteenth module for determining another set of two or more tentative patients whose patient identifiers most closely correlate to the patient specific data and the additional patient specific data, if the thirteenth module for comparing the patient specific data and the additional patient specific data to the stored patient identifiers identifies multiple patients;
   a sixteenth module for displaying the another set of tentative patients and their associated patient identifiers to facilitate a positive identification of the certain person;
   a seventeenth module for enabling the practitioner to attempt to positively identify the certain person from the displayed patient identifiers in the displayed another set of tentative patients;
   an eighteenth module for permitting access, in response to the certain person being positively identified, directly to the shared document repository on the centralized server system storing the medical record for the certain person being positively identified; and
   a nineteenth module for adding the certain person to the master index as a new patient, in response to the certain person not being positively identified.

22. The system of claim 21, wherein patient identifiers include fingerprint information.

23. The system of claim 21, wherein patient identifiers include demographic information.

24. The system of claim 21, further comprising a twentieth module for verifying the identity of the practitioner.

25. The system of claim 21, further including a twenty-first module for verifying the identity of the practitioner using fingerprint information.

26. The system of claim 21, further including a twenty-second module for arranging the shared document repository as a partitioned data base; a twenty-third module operatively connected to the data base for partitioning the data base among the plurality of facilities for the patient records associated with corresponding facilities.

27. The system of claim 21, further comprising a twenty-fourth module for selecting which of the plurality of facilities to operate a unified treatment plan system.

28. The system of claim 27, further comprising a twenty-fifth module for installing a treatment plan system on the server for a facility not selected to operate the unified treatment plan system.

29. The system of claim 27, further comprising a twenty-sixth module for installing a local treatment plan system at a facility not selected to operate the unified treatment plan system.

30. The system of claim 21, further comprising a twenty-seventh module for installing a unified treatment plan system on the server for each of the plurality of facilities.

* * * * *

UNITED STATES PATENT AND TRADEMARK OFFICE
CERTIFICATE OF CORRECTION

PATENT NO.         : 7,509,280 B1                                   Page 1 of 1
APPLICATION NO.    : 09/358355
DATED              : March 24, 2009
INVENTOR(S)        : Chris A. Haudenschild It is certified that error appears in the above-identified patent and that said Letters Patent is hereby corrected as shown below:

On the Title Page 1, Item (73), after Assignee: delete "ClinlComp" and insert
-- CliniComp --
Claim 8, column 13, line 53, delete "patent" and insert -- patient --
Claim 11, column 14, line 32, after "specific" delete ","
Claim 11, column 14, line 40, after "specific" delete ","
Claim 18, column 15, line 18, delete "patent" and insert -- patient --

Signed and Sealed this

Sixteenth Day of June, 2009

JOHN DOLL
*Acting Director of the United States Patent and Trademark Office*